United States Patent [19]

Barton et al.

[11] 4,064,148

[45] Dec. 20, 1977

[54] CHEMICAL PROCESS FOR PREPARING Δ9(11) DEHYDROSTEROIDS

[75] Inventors: Derek H. R. Barton, London, England; Robert H. Hesse, Cambridge, Mass.

[73] Assignee: Research Institute for Medicine and Chemistry Inc., Cambridge, Mass.

[21] Appl. No.: 688,714

[22] Filed: May 21, 1976

[30] Foreign Application Priority Data

May 22, 1975 United Kingdom ............... 22324/75

[51] Int. Cl.$^2$ ............................. C07J 5/00; C07J 3/00
[52] U.S. Cl. ................................................ 260/397.45
[58] Field of Search ..................................... 260/397.45

[56] References Cited

U.S. PATENT DOCUMENTS 3,728,337   4/1973   Barton .................... 260/239.55 D

*Primary Examiner*—Elbert L. Roberts
*Attorney, Agent, or Firm*—Bacon & Thomas

[57] ABSTRACT

The Specification describes a synthetic route for the preparation of a 9,11-dehydro-3-oxygenated 17α-hydroxy-20-ketopregnane which comprises the steps (i) electrophilically fluorinating a saturated 9,11-unsubstituted 3-oxygenated-17α-(esterified hydroxy)-20-ketopregnane, (ii) dehydrofluorinating the resulting 9α-fluorosteroid, if desired after transformations elsewhere in the molecule have been effected, and (iii) cleaving the ester group at the 17α-position to generate a 17α-hydroxy group.

15 Claims, No Drawings

CHEMICAL PROCESS FOR PREPARING Δ9(11) DEHYDROSTEROIDS

This invention is concerned with an improvement in or modification of the process of our Application Ser. No. 581283 filed May 27, 1975 wherein there is described a process for the electrophilic fluorination of a saturated organic compound (i.e. a compound wherein all the carbon-carbon linkages are saturated or wherein any carbon-carbon multiple bonds are substantially completely deactivated against electrophilic fluorination under the reaction conditions employed), said compound containing a hydrogen atom bound to a tertiary carbon atom, which comprises reacting together the said compound and an electrophilic fluorinating agent substantially homogenously dispersed in a liquid medium in the presence of a substance suppressing free radical reactions whereby formation of free fluorine radicals is suppressed and the said hydrogen atom is electrophilically replaced by a fluorine atom, the thus-obtained tertiary organic fluoride thereafter being recovered.

The process of our said Application is of considerable benefit by virtue of the selective nature of the fluorination, which is substantially confined to tertiary carbon atoms. Furthermore, the direction and rate of fluorination are strongly influenced by the electron densities about individual tertiary C-H bonds, so that it is possible to restrict the fluorination substantially completely to a single tertiary carbon atom by selection of a reaction substrate wherein the other tertiary C-H bonds are deactivated by, for example, closely proximate electron-withdrawing substituents.

One useful embodiment of the process lies in the preparation of 9α-fluoro derivatives of steroids substituted in the A and D rings by electron-withdrawing groups. Such groups tend to deactivate the 5- and 14-positions as regards electrophilic fluorination, and since the 8-position is inherently somewhat unreactive by virtue of the C-8 hydrogen atom being on the β-face of the molecule and so screened by the C-18 and C-19 methyl groups, electrophilic fluorination of ring A- and ring D- substituted steroids of this type proceeds substantially exclusively at the 9α-position.

A valuable application of this embodiment of the process occurs in the synthesis of corticosteriods, which generally possess an oxygen function, e.g. a hydroxyl group, at the 11-position. Thus it is possible to effect electrophilic fluorination of an appropriately substituted corticosteriod precursor having an unsubstituted C ring, to introduce a fluorine atom at the 9α-position; the 9α-fluorosteroid may thereafter be dehydrofluorinated to generate a $\Delta^{9,11}$ double bond. The resulting 9,11-dehydrosteroid may readily be reacted using conventional methods to introduce substituents at the 9- and/or 11-positions; thus, for example, the compound may be converted to an epoxide and then treated with hydrogen fluoride to yield the 9α-fluoro-11β-hydroxy analogue. This technique therefore provides a simple and convenient chemical method of use in the synthesis of a range of biologically active corticosteriods from readily available starting materials, for example saturated 9,11-unsubstituted pregnane derivatives, and may be contrasted with the more complicated synthetic techniques in current use, involving, for example, a microbiological hydroxylation reaction to functionalise the 11-position, or requiring the use of ring C-oxygenated precursor starting materials such as hecogenin.

Care must be taken in the preparation of 9,11-dehydrosteroids using the above-described electrophilic fluorination/dehydrofluorination technique to ensure that side reactions involving the ring A and ring D substituents are substantially avoided. Thus, for example, where it is desired to treat corticosteroid precursors such as 3-oxygenated 17α-hydroxy-20-ketopregnanes it is necessary to take steps to avoid rearrangement of the 17α-hydroxy-20-keto system, which will tend to occur during acid-catalysed or base-catalysed dehydrofluorination. While in principle it would appear that this particular problem could be avoided by selecting a 17α-unsubstituted pregnane starting material and subsequently hydroxylating at the 17α-position the 9,11-dehydrosteroid obtained by electrophilic fluorination/dehydrofluorination, it transpires that the absence of an electronegative substituent at the 17α-position in fact tends to enhance the susceptibility of the 14-position of the molecule to electrophilic fluorination so that it is no longer possible to achieve fluorination substantially exclusively at the 9α-position, the fluorination product being contaminated by a proportion of unwanted 14-fluoro compound where a 17α-unsubstituted pregnane starting material of the above-described type is used.

We have now found, however, that saturated 9,11-unsubstituted-3-oxygenated 17α-hydroxy-20-ketopregnanes may be electrophilically fluorinated/dehydrofluorinated in a particularly simple, efficient and convenient manner, to yield the corresponding 9,11-dehydrosteroid, if the 17α-hydroxy group is protected as an ester group in which the acid residue is both electronegative and readily cleavable. An especially preferred ester grouping for this purpose is the nitrate group.

Thus according to one aspect of the present invention there is provided a process for the preparation of a 9,11-dehydro-3-oxygenated-17α-hydroxy-20-ketopregnane which comprises the steps (i) electrophilically fluorinating a saturated 9,11-unsubstituted-3-oxygenated-17α-(esterified hydroxy)-20-ketopregnane wherein the acid residue in the ester group at the 17α-position is both electronegative and readily cleavable, by reacting said steroid and an electrophilic fluorinating agent substantially homogeneously dispersed in a liquid medium in the presence of a substance suppressing free radical reactions (hereinafter referred to as a "free radical inhibitor"), whereby formation of free fluorine radicals is suppressed and the 9α-hydrogen atom of said steroid is electrophilically replaced by a fluorine atom, (ii) dehydrofluorinating the resulting 9α-fluorosteroid, if desired after transformations elsewhere in the molecule have been effected, and (iii) cleaving the ester group at the 17α-position to generate a 17α-hydroxy group.

As indicated above, the ester group at the 17α-position of the steroid starting material is preferably a nitrate group, although ester groups such as trifluoroacetate or trichloracetate in which the acid residue is electronegative and easily cleaved may also be employed.

The oxygen function at the 3-position of the starting material may be a hydroxy, etherified hydroxy, esterified hydroxy or oxo group, or an oxo group protected as a ketal. Hydroxy and substituted hydroxy groups at the 3-position may posses the α- or β-configuration. It may be advantageous, as described in greater detail hereinafter, to employ a starting material having identical ester functions at the 3- and 17α-positions.

The starting material may carry other substituents characteristic of corticosteroids, for example a methyl group at the 16α- or 16β-position and/or an oxygen function, e.g. a hydroxy, etherified hydroxy or esterified hydroxy group, at the 21-position.

Starting materials useful in the present process thus include compounds of formula

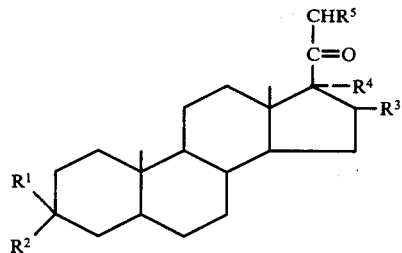

where $R^1$ represents hydroxy, etherified hydroxy (e.g. lower alkoxy, for example containing 1-6 carbon atoms, such as methoxy or ethoxy) or esterified hydroxy (e.g. lower alkanoyloxy such as acetoxy, lower haloalkanoyloxy such as trichloroacetoxy, especially perfluoro lower alkanoyloxy such as trifluoroacetoxy, aroyloxy such as benzoyloxy or nitrobenzoyloxy, or nitrooxy) and $R^2$ is hydrogen, or $R^1$ and $R^2$ together form an oxo group or represent an optionally cyclic ketal grouping; $R^3$ is hydrogen or methyl (α- or β-); $R^4$ is an esterified hydroxy group such as nitrooxy, trifluoroacetoxy or trichloroacetoxy in which the acid residue is electronegative and readily cleavable; and $R^5$ is hydrogen, hydroxy, etherified hydroxy or esterified hydroxy (e.g. as described for $R^1$ above).

The product of the electrophilic fluorination step (i) of the present process may, when a starting material of formula I is employed, be represented by the formula

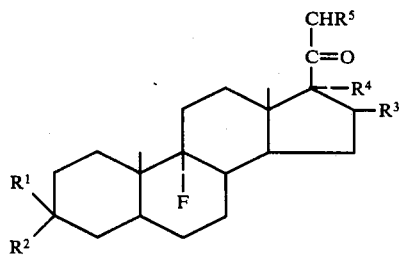

(where $R^1$, $R^2$, $R^3$, $R^4$ and $R^5$ have the above-defined meanings).

The compound (II) may if desired be subjected to other synthetic transformation, before or after the dehydrofluorination to generate the 9,11-double bond. Thus, for example, a compound in which $R^1$ is hydroxy or etherified or esterified hydroxy may be oxidised or deetherified/deesterified and then oxidised, to yield a 3-keto compound; a 3-keto compound may be brominated at the 2- and/or 4-positions and then dehydrobrominated to introduce double bonds at the 1- and/or 4-positions, whereafter the 3-keto group may, if desired, be reduced to a hydroxy group; and/or compounds in which $R^5$ is hydrogen may be functionalised at the 21-position, e.g. by bromination and treatment with acetate ion to introduce a 21- acetoxy group. Once the dehydrofluorination has been effected the ester group at the 17α-position may be cleaved to regenerate a hydroxy group.

Allowing for the above-mentioned possibilities of synthetic transformations, products which may be obtained in accordance with the process of the invention include compounds having the formula

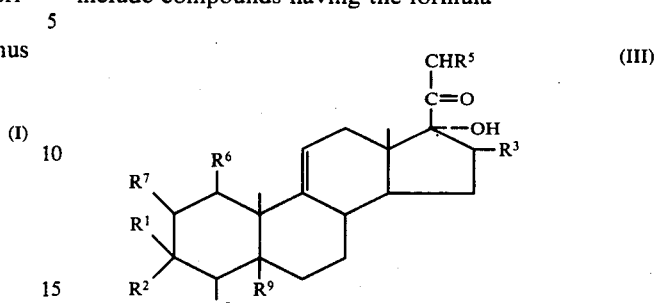

where $R^1$, $R^2$, $R^3$ and $R^5$ have the above-defined meanings, $R^6$ and $R^7$ are each hydrogen or together represent a carbon-carbon double bond, and $R^8$ and $R^9$ are each hydrogen or together represent a carbon-carbon double bond.

The fluorination step (i) in the process of the invention may be carried out in the manner described in our said copending Application.

Thus the electrophilic fluorinating agent may, for example, be a hypofluorite wherein the fluoroxy group is bonded to an inert electron attracting group, which may be either inorganic or organic. Suitable inorganic hypofluorites include fluorosulphur hypofluorites such as pentafluorosulphur hypofluorite. Organic hypofluorites which may be used include lower (e.g. $C_{1-6}$) fluoroalkyl hypofluorites, the fluoroalkyl portions of which preferably contain at least two fluorine atoms per carbon atom. Examples of such organic hypofluorites include trifluoromethyl, perfluoropropyl, perfluoroisopropyl, perfluoro-t-butyl, monochlorohexafluoropropyl and perfluoro-t-pentyl hypofluorites, and difluoroxy compounds such as 1,2-difluoroxytetrafluoroethane and difluoroxydifluoromethane. The use of trifluoromethyl hypofluorite is particularly preferred by virtue of its good selectivity and comparative ease of handling.

Elemental fluorine may also be employed as the electrophilic fluorinating agent in the process of the invention. Where fluorine is used in this way it is preferably either diluted with an inert gas such as nitrogen or argon, the concentration of fluorine in the resulting gas mixture conveniently being in the range 1-20% v/v, e.g. 3-6% v/v, or is introduced into the reaction system undiluted but at reduced pressure, e.g. less than 100 mm Hg, in order to moderate the reaction and facilitate control.

The fluorination is normally conducted in a solvent medium. The solvent need not be completely inert to the reaction conditions and in many cases will act as a free radical inhibitor as described in more detail hereinafter. Suitable solvents may include lower alkanoic acids such as acetic acid; fluorinated lower alkanoic acids such as trifluoroacetic acid; fluorinated or fluorinated and chlorinated lower alkanes such as fluorotrichloromethane, chlorotrifluoromethane, dichlorodifluoromethane or 1,1,2-trichlorotrifluoroethane; fluorinated lower alkanols such as 2,2,2,-trifluoroethanol; hydrates, e.g. the sesquihydrate, of hexafluoroacetone; nitriles such as acetonitrile; sulphones, e.g. di(lower alkyl)sulphones such as dimethylsulphone or cyclic sulphones such as sulpholane; and lower nitroalkanes such as nitromethane. Partially chlorinated lower alkanes such as chloroform or methylene chloride may also be employed as solvent, although such chloroalkanes have a tendency to react with the fluorinating reagent, which may therefore have to be used in excess to achieve optimum yields of the desired fluorinated product. Mixtures of solvents, e.g. fluorotrichloromethane and chloroform, may be used if desired. Cosolvents, e.g. water, lower alkanols or cyclic ethers such as dioxan or tetrahydrofuran, may also be employed. Some displacement of the newly introduced fluorine atoms by solvent molecules may occur when solvents such as alkanols and carboxylic acids, which contain nucleophilic centres are used, although this tendency is reduced if steps are taken, e.g. as described hereinafter, to remove the hydrogen fluoride normally formed as a by product of the fluorination reaction.

We have found that the efficiency of the fluorination reaction is greatly impaired unless steps are taken to ensure that the reaction mixture remains essentially homogeneous throughout the course of the reaction. Thus fluorinating agents such as gaseous or volatile liquid hypofluorites or fluorine/inert gas mixtures are advantageously passed into the reaction solution in gaseous form in such a way as to ensure good dispersion of the gas within the solution, for example by passage through a sintered dispersion tube or a perforated disc or foil. The reaction solution is also desirably stirred or otherwise agitated to enhance dispersion of the fluorinating agent through the solution. Hypofluorite reagents are generally highly soluble in the commonly employed reaction solvents, so that adequate dispersion of these reagents can be effected comparatively easily. Elemental fluorine has a substantially lower solubility, however, so that efficient dispersion of the fluorine/inert gas mixture as it enters the reaction solution and vigorous agitation of the solution are required to produce the desired degree of homogeneity in the solution.

Alternatively the fluorinating agent may be employed in solution, e.g. in one of the solvents listed above, or in liquid form, e.g. in the case of a liquid hypofluorite having comparatively low volatility; mixing of this fluorinating agent solution with the solution of the saturated organic compound is desirably accompanied by vigorous stirring.

The concentration of the reactants in the reaction solution is desirably kept comparatively low in order to ensure substantially homgeneous reaction conditions. Thus, for example, we prefer to employ comparatively dilute solutions of the steriod starting material, e.g. solutions containing 4-500 millimoles per litre of said compound. Similarly, where a gaseous hypofluorite reagent is employed it may be advantageous to admix this with an inert gaseous diluent such as nitrogen before its introduction into the reaction solution. The homogeneity of the reaction solution is further enhanced if the fluorinating agent is added slowly over a period of time, e.g. 2-24 hours, to a solution of the steroid.

The reaction temperature is preferably kept relatively low, the optimum temperature for a given reaction depending on, inter alia, the reactivity of the fluorinating agent. Hypofluorites, for example, may conveniently be employed at temperatures in the range $-78°$ to $+40°$ C; more reactive hypofluorites such as pentafluorosulphur hypofluorite may be used at lower temperatures within this range, whereas milder fluorinating agents such as trifluoromethyl hypofluorite may be employed at higher temperatures, e.g. in the range $-25°$ to $+25°$ C. Reactions involving elemental fluorine are generally conducted at somewhat lower temperatures, e.g. in the range $-100°$ to $0°$ C, conveniently at about $-75°$ C.

As indicated above, the fluorination is conducted in the presence of a free radical inhibitor in order to suppress competing free radical reactions which would detract from the selectivity and specificity of the electrophilic fluorination reaction. We have found oxygen to be a very effective free radical inhibitor for this purpose. In some cases oxygen will already be present in sufficient quantity in the reaction system, for example as a contaminant of nitrogen used to dilute a gaseous fluorinating agent or in solution in the reaction solvent, to inhibit any radical reactions; alternatively, sufficient radical inhibition may be achieved if the reaction is conducted in the presence of air, for example using a partially open reaction vessel. In other instances it may be desirable actually to introduce oxygen or air into the reaction system to obtain satisfactory radical inhibition.

Other free radical inhibitors which may be employed include nitro-substituted aromatic hydrocarbons, for example nitrobenzene or m-dinitrobenzene, and quinones, for example benzoquinone.

The amount and nature of the free radical inhibitor used in a given fluorination reaction will to some extent depend on the particular electrophilic fluorinating agent employed. Thus, for example, hypofluorites such as trifluoromethyl hypofluorite are somewhat more prone to free radical formation than molecular fluorine and may require larger quantities of inhibitor or the use of more potent inhibitors to suppress fully any radical reactions.

As indicated above, the reaction solvent may in certain cases act as a free radical inhibitor, as may any cosolvent used therewith. Thus, for example, solvents or cosolvents containing one or more reactive hydrogen atoms bound to carbon, for example partially chlorinated hydrocarbons such as chloroform or methylene chloride or cyclic ethers such as tetrahydrofuran, will suppress free radical reactions in cases wherein hypofluorites are employed as the fluorinating agent, although the degree of inhibition achieved in such solvents may be somewhat less than that obtained by the use of the above-described free radical inhibitors such as oxygen, nitrobenzene and benzoquinone. In cases where elemental fluorine is employed as the fluorinating agents, most solvents will have at least a partial inhibitory effect on any competing free radical reactions. This will generally be complemented by the inhibitory effect of traces of oxygen which will normally be present in the reaction system if it has not been purposely excluded, so that in many cases solution reactions using, for example, a fluorine/nitrogen gas mixture as the fluorinating agent may not in fact require the addition of a separate free radical inhibitor.

A side reaction which may accompany the fluorination process is elimination of the newly-introduced fluorine atom together with a hydrogen atom from an adjacent carbon atom, e.g. at the 11-position, with consequent formation of a carbon-carbon double bond. While the formation of a double bond is the ultimate object of the present process, double bond formation at this stage of the reaction sequence is undesirable, since the double bond will tend to be attacked by the fluorinating agent, leading to the formation of a range of unwanted fluorinated by-products.

The above-mentioned elimination of fluorine is catalysed by hydrogen fluoride, which is in most cases a by-product of the fluorination process; the elimination is also effectively autocatalytic since it is necessarily accompanied by the formation of hydrogen fluoride. Accordingly it is possible to suppress the elimination side reaction to a substantial degree if the fluorination process is carried out in the presence of a substance which will bind or adsorb hydrogen fluoride, for example a weak base (e.g. an alkali metal salt of an organic acid, for example a lower alkanoic acid such as acetic acid or a halogenated, preferably fluorinated, lower alkanoic acid such as trifluoroacetic acid, or an anhydrous alkali metal fluoride such as sodium or potassium fluoride), a dried and activated molecular sieve or an organosilicon compound which contains a bond to silicon that is easily cleaved by hydrogen fluoride to give a silyl fluoride and which is unreactive to the fluorinating agent (e.g. a siloxane such as hexamethyldisiloxane, a silyl ether such as methyl trimethylsilyl ether, a silyl ester such as trimethylsilyl acetate or a silylamide such as N,O-bis (trimethylsilyl) trifluoroacetamide). We prefer to use weak bases such as sodium trifluoroacetate or sodium or potassium fluoride as a basic hydrogen fluoride binding agent when a hypofluorite is employed as the fluorinating agent since stronger bases such as sodium or potassium acetate tend to promote decomposition of the hypofluorite, although such stronger bases are tolerated when for example, elemental fluorine is employed as fluorinating agent.

Crude reaction products obtained in the fluorination step of the process of the invention may also be prone to decompose by elimination of hydrogen fluoride in a similar manner to that described above, particularly when a hypofluorite fluorinating agent has been employed, the autocatalytic decomposition being initiated by hydrogen fluoride formed from the breakdown of impurities such as carbonyl difluoride. It may therefore be advantageous, where no base has been added previously, to add a base, for example a tertiary organic base such as pyridine or triethylamine, to the crude fluorinated product to bind any hydrogen fluoride which is liberated and so stabilise the product; such treatment is particularly desirable when there is to be any delay in the recovery and further reaction of the fluorinated product.

The dehydrofluorinatin step (ii) in the process of the invention may be effected in any convenient manner, for example using conventional techniques such as acid-catalysed or base-catalysed hydrolysis. A particularly satisfactory method of effecting dehydrofluorination is to treat the 9α-fluorosteriod with a fluorinated Lewis acid such as boron trifluoride, phosphorus trifluoride, phosphorus pentafluoride, antimony trifluoride, antimony pentafuoride or stannous fluoride, the use of boron trifluoride being preferred.

Dehydrofluorination is conveniently effected under anhydrous conditions e.g. in solution in a hydrocarbon solvent such as benzene, for example at ambient temperature.

Cleavage of the ester group at the 17α-position in step (iii) of the process may be effected by any means appropriate to the ester group which has been selected. It will be appreciated that the cleavage reaction should employ mild conditions which do not affect other sites in the molecule, unless this is desired for a particular purpose.

Where the 17α-ester group is a nitroxy group this may conveniently be removed by reductive cleavage, e.g. by treating a solution of the 9,11-dehydro steriod ester in an appropriate solvent, e.g. ethanol, with zinc in the presence of a weak acid such as ammonium acetate. Ester groups such as trichloroacetoxy and trifluoroacetoxy may be cleaved hydrolytically, for example under mildly basic conditions.

The 17α-ester group in the steriod starting material may, for example, be introduced using conventional esterification techniques. Thus a nitroxy group may be formed by reacting the steriod-17α-ol in an appropriate solvent, e.g. an acetic acid/acetic anhydride mixture, with fuming nitric acid; it may be advantageous to cool the steriod-17α-ol solution, e.g. to 0° C, prior to addition of the nitric acid.

As indicated above it may be advantageous to employ a steriod starting material having identical ester groups at the 3- and 17α-positions. Thus, for example, where the starting material is a 21-acetate it may be convenient to react a 3,17α-dinitrate derivative, since the two nitrooxy groups can readily and simultaneously be removed after the electrophilic fluorination/dehydrofluorination without disturbing the 21-acetate grouping. The resulting 9,11-dehydro-3,17α-dihydroxysteriod-21-acetate may, for example, then be oxidised to the corresponding 3-keto compound and brominated/dehydrobrominated to generate a 9,11-dehydro-17α-hydroxy-21-acetoxy-steriod-1,4-dien-3-one corticosteriod precursor.

The following example illustrates the invention

EXAMPLE

16β-Methyl-3β,17α,21-trihydroxy-5α-pregn-9(11)-en-20-one 3,21-diacetate a. 16β-Methyl-3α,17α,21-trihydroxy-5α-pregnan-20-one 3,21-diacetate-17-nitrate 16β-Methyl-3β,17α,21-trihydroxy-5α-pregnane-20-one 3,21-diacetate (4.5 g) was dissolved in acetic acid (100 ml), acetic anhydride (60 ml) was added, and the mixture was cooled to 0° C. 90% nitric acid (40 ml) was added in four portions and the mixture was allowed gradually to warm up to room temperature and was stirred overnight. The mixture was then poured into water (4 liters), stirred for 3–4 hours, and the resulting white precipitate was filtered off and washed several times with water. The precipitate was then dissolved in chloroform and the resulting solution was washed with water, dried and evaporated to low volume. Trituration with methanol precipitated the title compound (4.4 g, 90%); m.p. 126° C; $\eta_{max}$ 1755, 1740 (20 – keto, 3,21-diacetate) and 1640 cm$^{-1}$ (17α-nitrate); PMR spectrum includes signals at δ 4.63 (centre of ABq, J = 16 Hz, 21-CH$_2$OAc), 2.20 (s,C-21 acetoxy), 2.00 (s,C-3 acetoxy), 0.83 and 0.77 (C-18 and C-19 methyl).

b. 9α-Fluoro-16β-methyl-3β,17α,21-hydroxy-5α-prenan-20-one 3,21-diacetate-17-nitrate The title compound from (a) above (1.5 g) was dissolved in a mixture of chloroform (200 ml) and fluorotrichloromethane (250 ml) and sodium fluoride (ca. 2 g) and sodium trifluoroacetate (ca. 2 g) were added to the resulting solution. The solution was then cooled to −75° C and treated with 4 750cc bottles of fluorine diluted with nitrogen (each bottle contained 7 psi of fluorine diluted to 50 psi with nitrogen). The resulting reaction mixture was poured into aqueous sodium thiosulphate, and the organic phase was separated, washed twice with water, treated with 2-3 drops of pyridine, and dried over magnesium sulphate. The organic solvents were then evaporated to yield the crude title compound as a white solid. A sample recrystallised from methanol exhibited the spectral characteristics $\eta_{max}$ 1750 (wide bond, three carbonyl absorptions, and 1650 cm$^{-1}$ (17α-nitrate); PMR spectrum includes signals at δ 4.66 (centre of Abq, J = 16 Hz, 21-CH$_2$OAc, together with 3α-resonance), 2.17 (s, C-21 acetoxy), 2.00 (s, 3-acetoxy), 0.9 and 0.77 (C-18 and C-19 methyl); FMR φ* 179 (broad, J~80 Hz).

c. 16α-Methyl-3β,17α,21-trihydroxy-5α-pregn-9(11)-en-20-one 3,21-diacetate-17-nitrate A half of the crude product from (b) above was dissolved in dry benzene and treated with boron trifluoride diethyl etherate (1.1 ml). The resulting mixture was stirred overnight, a deep violet colour developing during this time. The solution was then poured into aqueous sodium bicarbonate, whereupon the violet colour disappeared. The organic phase was separated, washed with water and dried, whereafter the benzene was evaporated to yield the crude title compound as a yellow solid. This product showed one spot, less polar than the starting material, on t.l.c. (eluting with 17% ethyl acetate in hexane), the spot having a weak tail. The product was purified by liquid chromatogrpahy (using 15% ethyl acetate in cyclohexane ) to give purified title compound (380 mg, 50% overall from 16β-methyl-3β,17α,21-trihydroxy-5α-pregnan-20-one 3,21-diacetate-17-nitrate); single spot one t.l.c. $\eta_{max}$ 1760, 1750 (20-keto, 3,21-diacetate) and 1650 cm$^{-1}$ (17-nitrate); PMR spectrum includes signals at δ 5.34 (1H, narrow m, J$^h$/2 = 9 Hz, 11-H), 4.70 (3H, ABq, J = 16 Hz, 21-CH$_2$OAc together with 3α-H resonance), 2.17 (s, C-21 acetoxy), 2.00 (s, C-3 acetoxy), 0.95 and 0.68 (C-18 and C-19 methyl).

d. 16β-methyl-3β, 17α,31-trihydroxy-5α-pregn-9(11)-en-20-one 3,21-diacetate

The purified product from (c) above (205 mg) was dissolved in ethanol (ca. 60 ml) and ammonium acetate (ca. 2 g) and zinc (ca. 2 g) were added. The mixture was stirred at room temperature for 3 hours, whereupon the solvent was evaporated and the solid residue was dissolved in a mixture of water and chloroform. The organic phase was separated, washed with water and dried, whereafter the chloroform was evaporated to yield the title compound (175 mg, 95%) which showed a single spot on t.l.c. (30% ethyl acetate in hexane). A sample recrystallised from methanol exhibited m.p. 195°–6° C; $\eta_{max}$(Nujol) 3700 (17α-OH), 1770, 1750, and 1740 cm$^{-1}$ (20-keto, 3,21-diacetate); PMR spectrum includes signals at δ 5.33 (1 H, narrow m, J$^h$/2 = 9 l Hz, 11-H), 4.94 (2H, s, 21-CH$_2$OAc), 4.63 ( b 1 H, m, 3α-H), 2.17 (s, C-21 acetoxyl, 2.00 (s, C-3 acetoxyl, 0.97 and 0.70 (C-18 and C-19 methyl).

We claim:

1. A process for electrophilically fluorinating a saturated 9,11-unsubstituted-3-oxygenated-17α-(esterified hydroxy)-20-ketpregnane steriod wherein the esterified hydroxy group at the 17α-position is a nitrooxy, trifluoroacetoxy or trichloroacetoxy group, which comprises reacting said steriod and a fluorinating agent, wherein the fluorinating agent is molecular fluorine, a fluorosulphur hypofluorite or a C$_{1-6}$ fluoroalkyl hypofluorite; substantially homogeneously dispersed in a liquid medium in the presence of a free radical inhibitor whereby formation of free fluorine radicals is suppressed and the 9α-hydrogen atom of said steriod is replaced by a fluorine atom.

2. A process as claimed in claim 1 wherein the said steriod contains a hydroxy, etherified hydroxy, esterified hydroxy, oxo or ketal group in the 3-position.

3. A process as claimed in claim 1 wherein the resulting 9α-fluorosteriod is dehydrofluorinated.

4. A process as claimed in claim 3 wherein the said 9α-fluorosteriod is subjected to functional transformations elsewhere in the molecule prior to dehydrofluorination.

5. A process as claimed in claim 3, wherein the dehydrofluorination is effected by acid- or base-catalysed hydrolysis.

6. A process as claimed in claim 3 wherein the 17α-(esterified hydroxy)- group in the resulting compound is a nitrooxy group which is then subjected to reduction to generate a 17α-hydroxy group.

7. A process for the preparation of a 9,11-dehydro-3-oxygenated-17α-hydroxy-20-ketopregnane which comprises the steps (i) fluorinating a saturated 9,11-unsubstituted-3-oxygenated-17α-(esterified hydroxy)-20-ketopregnane wherein the esterified hydroxy group at the 17α-position is a nitrooxy, trifluoroacetoxy or trichloroacetoxy group, which comprises reacting said steriod and a fluorinating agent, wherein the fluorinating agent is molecular fluorine, a fluorosulphur hypofluorite or a C$_{1-6}$ fluoroalkyl hypofluorite; substantially homogeneously dispersed in a liquid medium in the presence of a free radical inhibitor, whereby formation of free fluorine radicals is suppressed and the 9α-hydrogen atom of said steriod is replaced by a fluorine atom, (ii) dehydrofluorinating the resulting 9α-fluorosteriod, and (iii) cleaving the ester group at the 17α-position to generate a 17α-hydroxy group.

8. The process of claim 7 wherein the 9α-fluorosteriod is subjected to functional transformations elsewhere in the molecule prior to dehydrofluorination.

9. The process of claim 2 wherein the starting material has identical ester functions at the 3 and 17α-positions.

10. A process as claimed in claim 1 wherein the fluorosulphur hypofluorite is pentafluorosulphur hypofluorite.

11. A process as claimed in claim 1 wherein the fluorinating agent is an organic hypofluorite selected from the group consisting of trifluoromethyl hypofluorite, perfluoropropyl hypofluorite, perfluoroisopropyl hypofluorite, perfluoro-t-butyl hypofluorite, monochlorohexafluoropropyl hypofluorite and perfluoro-t-pentyl hypofluorite.

12. A process as claimed in claim 11 wherein the hypofluorite is trifluoromethyl hypofluorite.

13. A process as claimed in claim 2 wherein the fluorinating agent is molecular fluorine which is diluted with an inert gas, wherein the inert gas is nitrogen or argon, to a concentration of from 1–20% v/v, or is undiluted but introduced at a reduced pressure of less than 100 mm Hg.

14. A process as claimed in claim 1 wherein the steriod which is fluorinated is present in an amount of from 4–500 millimoles per litre.

15. A process as claimed in claim 3 wherein the 17α-(esterified hydroxy)- group in the resulting compound is a trifluoroacetoxy or trichloroacetoxy group which is then subjected to hydrolysis.

* * * * *